(12) United States Patent
Mackovic-Basic

(10) Patent No.: US 9,186,218 B2
(45) Date of Patent: Nov. 17, 2015

(54) LABORING PATIENT DIGNITY POO POUCH

(71) Applicant: Miriam Mackovic-Basic, Rancho Palos Verdes, CA (US)

(72) Inventor: Miriam Mackovic-Basic, Rancho Palos Verdes, CA (US)

(73) Assignee: Miriam Mackovic Basic, Rancho Palos Verdes, CA (US)

( * ) Notice: Subject to any disclaimer, the term of this patent is extended or adjusted under 35 U.S.C. 154(b) by 436 days.

(21) Appl. No.: 13/666,590

(22) Filed: Nov. 1, 2012

(65) Prior Publication Data

US 2014/0116448 A1    May 1, 2014

(51) Int. Cl.
*A61B 19/00* (2006.01)
*A61B 19/08* (2006.01)
*A61F 5/451* (2006.01)

(52) U.S. Cl.
CPC .............. *A61B 19/087* (2013.01); *A61F 5/451* (2013.01); *A61B 2019/085* (2013.01)

(58) Field of Classification Search
CPC .............. A61F 13/512; A61F 13/511; A61F 2013/51178; A61F 13/15707; A61F 13/2068; A61F 13/8405; A61F 2013/51007; A61F 2013/51344; A61F 5/445; A61F 5/448; A61F 13/472; A61F 2013/51355; A61F 5/005; A61F 5/0053; A61F 5/0003; A61F 13/51104
USPC ........................... 128/849, 856; 604/347–353
See application file for complete search history.

(56) References Cited

U.S. PATENT DOCUMENTS

| | | | | |
|---|---|---|---|---|
| 3,288,135 | A * | 11/1966 | Pereny et al. | 128/853 |
| 4,520,807 | A * | 6/1985 | Rotter | 128/849 |
| 4,570,628 | A * | 2/1986 | Neal | 128/853 |
| 2002/0040498 | A1 * | 4/2002 | Sloan et al. | 4/315 |

* cited by examiner

*Primary Examiner* — Michael Brown
(74) *Attorney, Agent, or Firm* — Vesna N. Rafaty

(57) ABSTRACT

A disposable device for containing stool from a laboring patient on an operating table comprising a flexible bag portion comprising an open end, the open end comprising an integral curvilinear attachment portion comprising means for manually securely attaching the device to the area above the perineum and around the rectum of the patient.

6 Claims, 2 Drawing Sheets

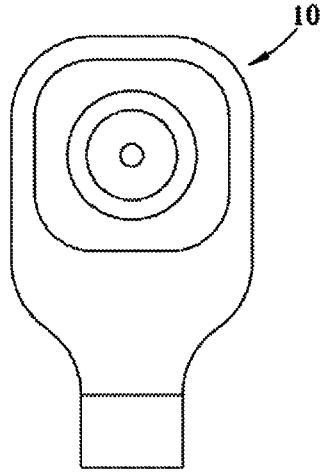
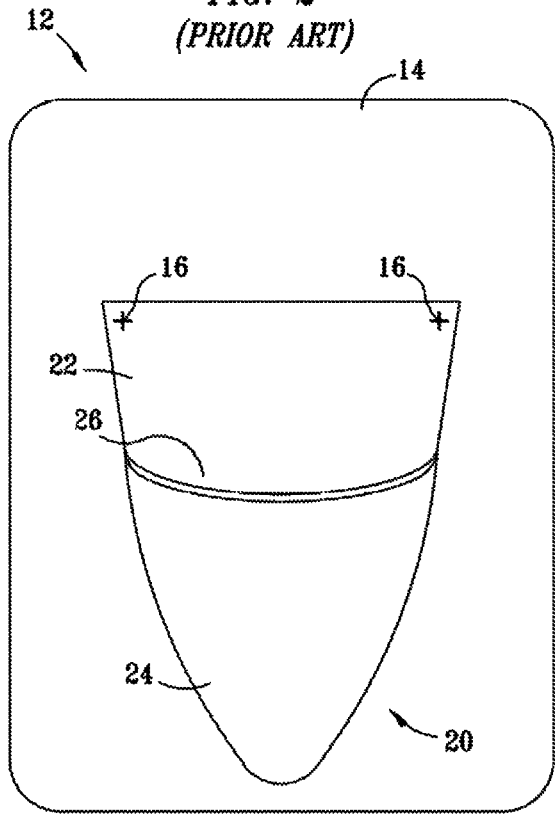
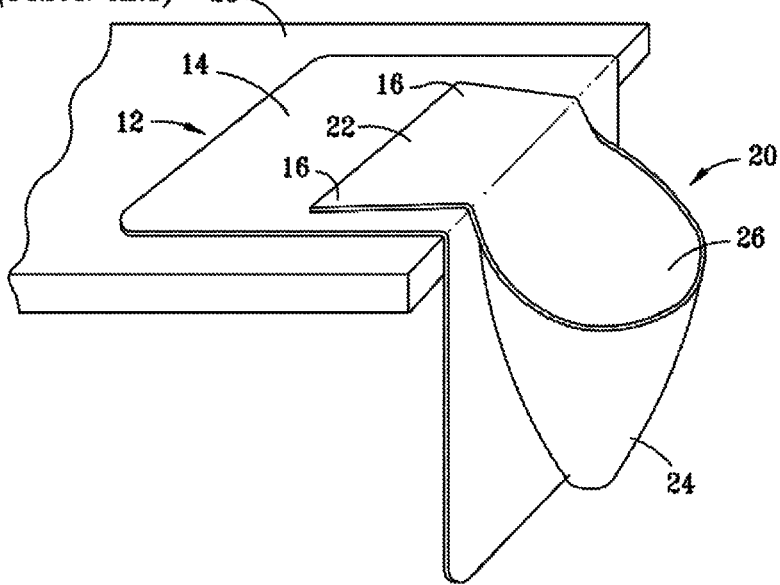
FIG. 1 (PRIOR ART)
FIG. 2 (PRIOR ART)
FIG. 3 (PRIOR ART)

LABORING PATIENT DIGNITY POO POUCH

CLAIM OF PRIORITY

This Non-Provisional Patent Application claims priority to and incorporates in full by reference the named sole inventor's Provisional Patent Application No. 61/554,221 entitled "Laboring Patient Dignity Poo Pouch" e-filed on Nov. 1, 2011.

BACKGROUND OF THE INVENTION

The disclosed invention is directed to disposable devices for the efficient, dignity capture of stool from a laboring patient lying or an operating table, Stoma (ostomy) bags are known (see for example http://www.totalhomecaresupplies.com/CategoryDetail.aspx?CategoryName=OS TOMY). Devices for helping to control anal incontinence are known. See for example U.S. Pat. No. 7,794,385 to Rosenblatt entitled "System and method for treatment of anal incontinence and pelvic organ prolapse." Bedpan systems are known (see for example U.S. Publication 20100125951 entitled "Bedpan system"). Shower systems with 'dignity mat' are known (see for example U.S. Publication 20090019631 entitled "Shower chair dignity mat"). Absorbent articles that help to protect the wearer's skin, protect against leakage, or that modify the feces via a feces modification agent are known (see for example U.S. Publication 70100774209 entitled "Disposable article providing improved management of bodily exudates"). Known barrier drapes used in the operating room have an attached transparent bag with a large opening for the collection of feces and other exudates from the body of the patient and are not attached to the rectum, thus leaving the rectum exposed and without a cover. As a result, the prior art drapes allow uncontrolled dispersion of portions of the stool which is unpleasant for the patient and medical personnel alike. The applicant is not aware of a prior art device designed for attachment to the perineum around the rectum area for the controlled capture and containment of a stool from a laboring patient.

SUMMARY OF THE INVENTION

Worldwide there are currently roughly 140 million deliveries per year. A laboring patient is concerned about the lack of control of the bowel. During a vaginal delivery, at least thirty percent of patients pass a stool during the second stage of labor. Embarrassed by the possibility of defecation, laboring patients sometimes try to stop pushing the baby in order to prevent defecation. The cleaning and removal of stool from the patient's body and surrounding operating table area are displeasing to the medical personnel. Contamination by feces can also occur to the body of the baby. Containing and preventing spread of feces will benefit the medical personnel and the baby. Removing the patients concern over defecation will facilitate a more efficient and safe delivery and a less stressful experience for the patient. The applicant has invented a device, herein called for convenience and not by way of limitation a laboring patient disposable dignity poo pouch (or, interchangeably, simply poo pouch), which in use is manually attached to the patient generally in the area of the rectum and is designed to capture and contain a stool while generally covering the area of the rectum to create a barrier.

Disclosed is as disposable poo pouch for capture of a tool from a laboring patient lying on an operating table. The poo pouch comprises a flexible, non-transparent plastic bag or pouch portion having an open end, and an integral attachment portion. The bag portion comprises a substantially cylindrical, elongated bag made of flexible opaque material such as but not limited to plastic or other suitable material. The attachment portion, designed for manual, removable attachment just above and around the rectum is curvilinear, preferably elliptical or semi-circular, to accommodate the patient's anatomy in the area around the rectum. The curvilinear end of the attachment portion comprises an adhesive applied to segments or optionally the entirety of the curvilinear end facilitating attachment to the patient. The attachment portion is preferably comprised of stretchable and flexible adhesive-backed material to flex with the movement of the patient during labor. The portion of the attachment arch closest to the perineum may optionally be more tensile rigid to provide support to the perineum during labor with intention of lowering the risk of tearing. The top end of the attachment portion is placed on the perineum above the rectum. The left and right sides of the curvilinear attachment portion are applied on the inner side of the left and right sides of the gluteal muscles of the patient. The poo pouch further comprises an integral drape or flap portion contiguous with a portion of the open end of the bag portion. The patient's buttocks rest on the drape portion.

Per an alternative embodiment, the bottom end of the attachment portion is adhered to the area below the patient's rectum and buttocks near the patient's lower back. With the poo pouch attached as described, the bag portion, the attachment portion and the drape portion create a substantial enclosure around the rectum for a controlled capture of the stool passed by the patient during labor.

After labor, the poo pouch is gently detached from the patient's skin by pulling on the attachment portion and the poo pouch and its contents are discarded. Optionally, the removal process may comprise hypoallergenic adhesive remover. The poo pouch may optionally be scented to help manage the odor with a defecating patient or it may be adapted to be odor-absorbing. The poo pouch can be sold as a standalone device or pre-attached to a conventional barrier drape used in the labor operating room. The poo pouch may be offered in varying sizes to accommodate the spectrum of body sizes and shapes. The adhesive used in the curvilinear attachment portion preferably is safe for use on human skin and will not irritate the delicate and sensitive skin of the patient in the general area of the rectum. The adhesive should be strong enough to securely adhere the poo pouch to the patient when the poo pouch contains stool and to allow for patient movement and flexibility incumbent during labor.

The disclosed poo pouch may be offered and sold as a standalone product or as a component in a kit comprising a surgical drape.

BRIEF DESCRIPTION OF THE DRAWINGS

FIG. 1 is a perspective of a prior art ostomy bag

FIG. 2 is a perspective of a prior art barrier drape with an attached bag for collection of feces FIG. 3 shows the prior art drape placed on an operating table

DETAILED DESCRIPTION OF THE DRAWINGS

Figure 4:
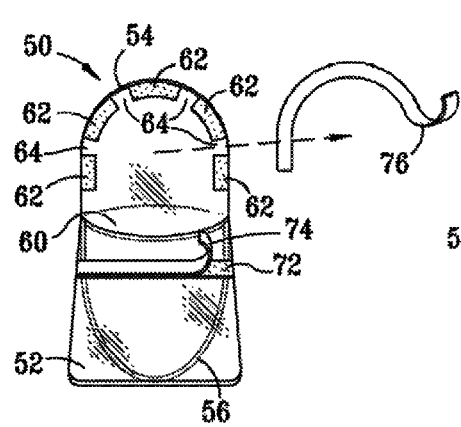
FIG. 4 is a front perspective of a preferred embodiment of the disclosed poo pouch

FIG. 1 is a prior art ostomy bag 10 designed to be worn by a patient.

FIG. 2 is a prior art barrier drape 12 with an attached feces collection bag 20. The prior art device comprises a rectangular drape sheet portion 14 placed underneath the patient's buttocks, a flexible bag portion 20 attached to the rectangular drape sheet 14 and having an open top 26. FIG. 3 shows the prior art device in use on a patient operating table (patient not shown).

Figure 5:
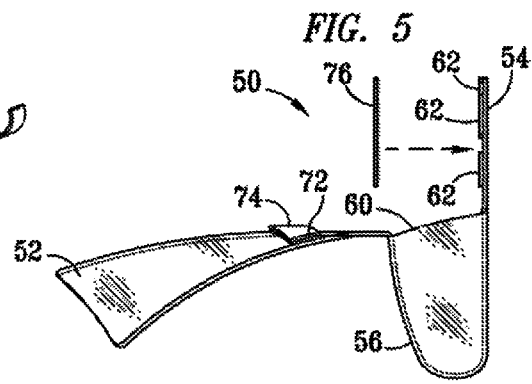
FIG. 5 is a side perspective of the preferred embodiment of the poo pouch

FIG. 4 shows a preferred embodiment of the disclosed poo pouch 50 composing an opaque flexible bag or pouch portion 56, a drape portion 52, and an attachment portion 54. The attachment portion 54 comprises alternating stretchable segments 64 and non-stretchable, adhesive-backed portions 62. During application of the poo pouch 50, the removable tab 76 is peeled away from the poo pouch attachment portion 54 to expose the adhesive of the attachment portion 54. The drape portion comprises an attachment portion 72, 74. FIG. 5 is a side perspective of the disclosed preferred embodiment of a poo pouch 50 showing the drape portion 52 and the drape portion attachment portion 72,74 for securement of the drape portion to the patient's buttocks 40.

Figure 6:
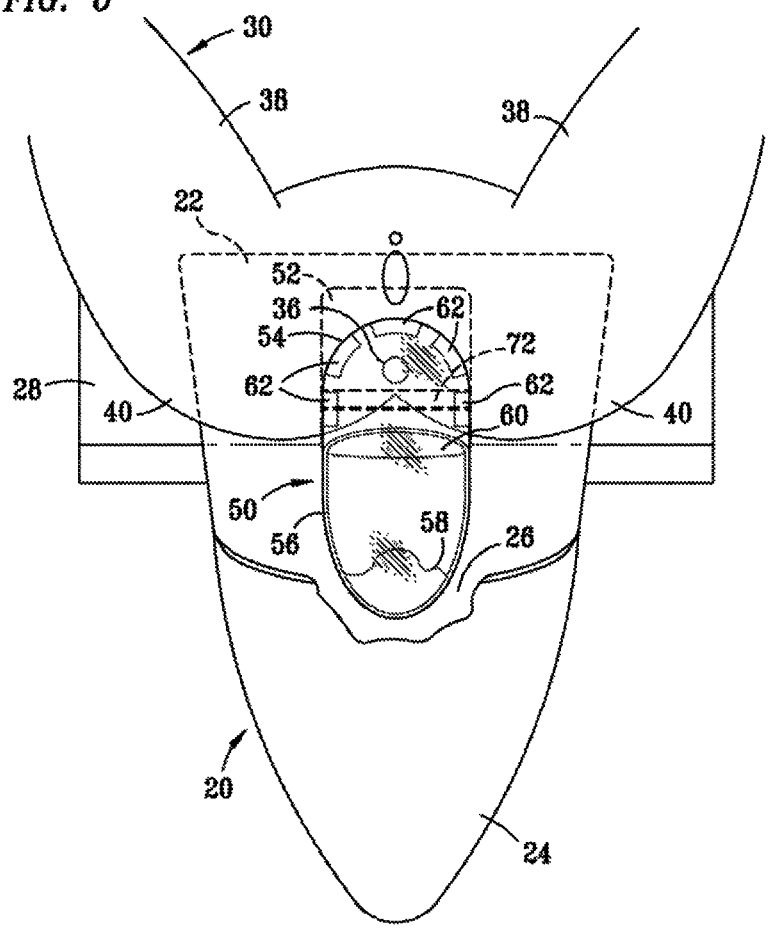
FIG. 6 is a front perspective of the poo pouch in use and placed on the laboring patient

FIG. 6 shows the poo pouch 50 in use as part of and in combination with a prior art barrier drape 20. The poo pouch 50 is placed on the patient 30 with the attachment portion 54 adhered to the area (perineum) just above the patient's rectum 36 and below the vaginal opening. The attachment portion 54 is shaped to generally frame the top and sides of the rectum. The preferred embodiment may have a substantially elliptical or semi-circular-shaped attachment portion 54. The attachment portion 54 has ends that have alternating stretchable, non-adhering segments 64 and sticky (adherable) segments 62. The purpose of the stretchable segments 64 that don't have adhesive is to allow the medical personnel to adjustably attach the poo pouch to patients of different sizes and to accommodate any tissue stretching during delivery. Once placed properly on the patient, with the patient's buttocks 40 resting on the drape portion 52 of the poo pouch, the bag portion 56 and the attachment portion 54 cooperate to create a cover for the rectum and a hence a barrier designed to capture the stool and prevent splash. Shown in FIG. 6 is an optional adhesive system (72/74) for secured attachment of the drape portion 54 of the poo pouch 50 to the area under each of the gluteal muscles or buttocks 40.

It is further noted that the attachment portion 54 of the poo pouch may optionally comprise a portion that is made of extra strong, high tensile strength material that can support the rectal muscle and potentially decrease the risk of rectal tear by adding support to the skin just above the rectum and on the sides of the rectum.

I claim:

1. A disposable device for containing stool from a laboring patient on an operating table comprising a flexible bag portion comprising an open end, the open end comprising an integral curvilinear attachment portion comprising connection means for securely attaching the device to the area above the perineum and around the rectum of the patient, further comprising an integral drape portion integral with the open end of the bag portion and extending opposite the attachment portion, the drape portion is adapted for placement under the patient buttock, the curvilinear portion comprises segments that are stretchable and segments that are non-stretchable.

2. The disposable device per claim 1 wherein the attachment portion comprises a continuous adhesive adapted for removable attachment of the attachment portion to the skin of the patient.

3. A disposable device for containing stool from a laboring patient on an operating table comprising a flexible bag portion comprising an open end, the open end comprising an integral curvilinear attachment portion comprising connection means for securely attaching the attachment portion to the area above the perineum of the patient, the open end further comprising an integral drape portion substantially opposite the attachment portion, the drape portion adapted for placement under the patient's buttocks and removable attachment to the patient's buttocks, the curvilinear attachment portion comprising segments that are non-stretchable and are stretchable and segments that have a rigid tensile strength.

4. A method for containment of feces passed by a laboring patient comprising steps of
Providing a disposable device comprising a flexible bag portion comprising an open end, the open end of the bag portion comprising an integral curvilinear attachment portion comprising connection means for securely attaching the pouch to the area above the perineum and around the rectum of the patient, the open end further comprising an integral drape portion substantially opposite the attachment portion,
Manually attaching the attachment portion to the patient's body in the area above the perineum and around the rectum,
Manually attaching the drape portion to the patient's buttocks, the hag portion, the attachment portion and the drape portion creating a substantial enclosure for containment of feces passed by the laboring patient said curvilinear attachment portion comprising segments that are stretchable and segments that are non-stretchable.

5. A kit comprising a surgical drape and a disposable device for containing stool from a laboring patient on an operating table, the device comprising an open end, the open end comprising an integral curvilinear attachment portion comprising connection means for securely attaching the device to the area above the perineum around the rectum of the laboring patient, further comprising an integral drape portion integral with the open end of the bag portion and extending opposite the attachment portion, the drape portion is adapted for placement under the patient buttock, the curvilinear portion comprises segments that are stretchable and segments that are non-stretchable.

6. A kit comprising a surgical drape, a disposable device for containing stool from a laboring patient removably attached to the surgical drape, the disposable device comprising a flexible bag portion comprising an open end, the open end comprising an integral curvilinear attachment portion comprising connection means for securely attaching the device to the area above the perineum and around the rectum of the laboring patient lying on an operating table, further comprising an integral drape portion integral with the open end of the bag portion and extending opposite the attachment portion, the drape portion is adapted for placement under the patient buttock, the curvilinear portion comprises segments that are stretchable and segments that are non-stretchable.

* * * * *